(12) United States Patent
Uno et al.

(10) Patent No.: US 9,915,620 B2
(45) Date of Patent: Mar. 13, 2018

(54) ABNORMALITY DETECTION SYSTEM AND ABNORMALITY DETECTION METHOD

(71) Applicant: FUJITSU LIMITED, Kawasaki-shi, Kanagawa (JP)

(72) Inventors: Kazushi Uno, Atsugi (JP); Fumio Takei, Isehara (JP); Takeo Kasajima, Machida (JP); Kyoko Tadaki, Atsugi (JP); Minoru Ishinabe, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 392 days.

(21) Appl. No.: 14/693,246

(22) Filed: Apr. 22, 2015

(65) Prior Publication Data

US 2015/0226679 A1 Aug. 13, 2015

Related U.S. Application Data

(63) Continuation of application No. PCT/JP2012/077350, filed on Oct. 23, 2012.

(51) Int. Cl.
*G01N 21/95* (2006.01)
*G01L 1/24* (2006.01)
(Continued)

(52) U.S. Cl.
CPC .............. *G01N 21/95* (2013.01); *G01B 11/16* (2013.01); *G01D 5/35364* (2013.01);
(Continued)

(58) Field of Classification Search
CPC ........ G01N 21/95; G01N 21/47; G01N 25/72; G01N 2201/08; G01B 11/16;
(Continued)

(56) References Cited

U.S. PATENT DOCUMENTS 5,113,277 A 5/1992 Ozawa et al.
5,639,162 A 6/1997 Sai
(Continued)

FOREIGN PATENT DOCUMENTS

DE 4019980 A1 1/1991
JP 02-123304 5/1990
(Continued)

OTHER PUBLICATIONS

Farahani et al., Spontaneous Raman Scattering in Optical Fibers with Modulated Probe Light for Distributed Temperature Raman Remote Sensing, Aug. 1999, Journal of Lightwave Technology, vol. 17, No. 8, pp. 1379-1391.*
(Continued)

*Primary Examiner* — Toan Le
(74) *Attorney, Agent, or Firm* — Staas & Halsey LLP

(57) ABSTRACT

An abnormality detection system includes an optical fiber, a Raman scattered light detection unit, and a data processing unit. The detection unit is configured to detect Stokes light and anti-Stokes light which are generated in the optical fiber and to output data on the intensity distribution of the Stokes light in the optical fiber in the length direction thereof and data on the intensity distribution of the anti-Stokes light in the optical fiber in the length direction. The processing unit is configured to calculate the product of a value obtained by applying an FIR filter to the intensity distribution of the Stokes light, and a value obtained by applying the FIR filter to the intensity distribution of the anti-Stokes light for each of locations on the optical fiber in the length direction, and to determine whether or not abnormality is present based on the result of the calculation.

17 Claims, 15 Drawing Sheets

(51) Int. Cl.
*G01K 11/32* (2006.01)
*G01D 5/353* (2006.01)
*G01B 11/16* (2006.01)
*G01N 21/47* (2006.01)
*G01N 25/72* (2006.01)

(52) U.S. Cl.
CPC .............. *G01K 11/32* (2013.01); *G01L 1/24* (2013.01); *G01N 21/47* (2013.01); *G01N 25/72* (2013.01); *G01N 2201/08* (2013.01); *G01N 2201/12* (2013.01)

(58) Field of Classification Search
CPC ............. G01D 5/35364; G01D 5/3537; G01D 5/35374; G01K 11/32; G01K 11/322; G01K 11/324; G01L 1/24; G01L 1/247
See application file for complete search history.

(56) References Cited

U.S. PATENT DOCUMENTS

| | | |
|---|---|---|
| 5,731,869 A | 3/1998 | Minami |
| 5,765,948 A | 6/1998 | Sai |
| 5,825,804 A | 10/1998 | Sai |
| 9,528,860 B2 * | 12/2016 | Uno ..................... G01K 11/32 |
| 2012/0033709 A1 | 2/2012 | Kasajima et al. |
| 2013/0215930 A1 | 8/2013 | Kasajima et al. |

FOREIGN PATENT DOCUMENTS

| | | |
|---|---|---|
| JP | 06-201488 | 7/1994 |
| JP | 7-55332 | 3/1995 |
| JP | 08-247858 | 9/1996 |
| JP | 09-018428 | 1/1997 |
| JP | 2812049 | 10/1998 |
| JP | 2006-023260 | 1/2006 |
| JP | 2006-168458 | 6/2006 |
| JP | 2010-223831 | 10/2010 |
| JP | 2011-209226 | 10/2011 |
| JP | 2011-232138 | 11/2011 |
| WO | WO 2010/125712 A1 | 11/2010 |
| WO | WO 2012/056567 A1 | 5/2012 |

OTHER PUBLICATIONS

International Search Report dated Dec. 4, 2012 in corresponding international application PCT/JP2012/077350.

Extended European Search Report dated Oct. 15, 2015 in corresponding European Patent Application No. 12887193.6.

* cited by examiner

| TIME | LOCATION (m) | LOSS BY PEAK (dB) | LOSS BY LINEAR APPROXIMATION (dB) | ACCURACY (%) |
|---|---|---|---|---|
| 2012/5/20 23:30 | 74.5 | 0.091 | | |
| 2012/6/2 6:55 | 80 | 0.037 | 0.035 | 99.94 |
| 2012/7/12 13;15 | 85 | 0.109 | 0.113 | 99.91 |
| 2012/8/20 14:31 | 122 | 0.045 | | |

| PEAK | LOCATION (m) | PEAK VALUE | AVERAGE LOSS (RATIO) |
|---|---|---|---|
| P1 | 74.5 | 183.3 | 0.018498 |
| P2 | 80 | 75.7 | 0.008095 |
| P3 | 85 | 219.5 | 0.025518 |
| P4 | 122 | 90.87 | 0.013078 |

FIG. 21

| PEAK | LOCATION (m) | PEAK VALUE (dB) | AVERAGE LOSS (dB) |
|---|---|---|---|
| P1 | 74.5 | 0.091 | 0.081 |
| P2 | 80 | 0.037 | 0.035 |
| P3 | 85 | 0.109 | 0.112 |
| P4 | 122 | 0.045 | 0.057 |

FIG. 22

| PEAK | LOCATION OF LEFT HALF OF FULL WIDTH AT HALF MAXIMUM (m) | LOCATION OF RIGHT HALF OF FULL WIDTH AT HALF MAXIMUM (m) | LF(m) | LR(m) |
|---|---|---|---|---|
| P1 | 73.5 | 75 | 72.5 | 76 |
| P2 | 79.25 | 80.75 | 78.25 | 81.75 |
| P3 | 84.25 | 86 | 83.25 | 87 |
| P4 | 120.75 | 122.75 | 119.75 | 122.75 |

FIG. 23

| PEAK | PaveN | $P_{N-1}$ to $P_N$ | $P_N$ to $P_{N+1}$ |
|---|---|---|---|
| P2 | 14808.3 | 14857.600 | 14739.400 |
| P3 | 14577 | 14768.000 | 14395.000 |

FIG. 24

| PEAK | LOCATION (m) | LOSS BY LINEAR APPROXIMATION (dB) | AVERAGE LOSS (dB) |
|---|---|---|---|
| P2 | 80 | 0.035 | 0.035 |
| P3 | 85 | 0.113 | 0.112 |

ABNORMALITY DETECTION SYSTEM AND ABNORMALITY DETECTION METHOD

CROSS-REFERENCE TO RELATED APPLICATION

This application is a continuation of International Patent Application No. PCT/JP2012/077350 filed on Oct. 23, 2012 and designated the U.S., the entire contents of which are incorporated herein by reference.

FIELD

The embodiments discussed herein are related to an abnormality detection system and an abnormality detection method.

BACKGROUND

In facilities such as chemical plants, oil refinery plants, and thermal power plants which use large amounts of flammable, explosive, or hazardous materials, it is important to detect corrosion and thinning on pipes and tanks at early stages to prevent serious accidents.

To do so, an abnormality detection system is sometimes employed which includes a temperature distribution measurement apparatus (distributed temperature sensor: DTS) configured to use an optical fiber as a temperature sensor.

This type of abnormality detection system has an optical fiber laid around a pipe or tank, for example, and the optical fiber's end is connected to the temperature distribution measurement apparatus. Then, laser is applied into the optical fiber from the temperature distribution measurement apparatus, and Raman scattered light generated inside the optical fiber is detected with the temperature distribution measurement apparatus to acquire the temperature of the pipe or tank, and the presence of abnormality is determined based on the obtained result.

In facilities such as chemical plants, oil refinery plants, and thermal power plants, a delay in abnormality detection may lead to serious accidents. Thus, a system capable of detecting the occurrence of abnormality at an even earlier stage is desired.

Note that the following patent documents disclose a technique related to the present application.

Patent Document 1: Japanese Laid-open Patent Publication No. 09-18428
Patent Document 1: Japanese Laid-open Patent Publication No. 02-123304
Patent Document 3: International Patent Pamphlet No. WO 2010/125712

SUMMARY

According to one aspect of a technique disclosed herein, there is provided an abnormality detection system, including: an optical fiber; a Raman scattered light detection unit configured to detect Stokes light and anti-Stokes light which are generated in the optical fiber and to output data on an intensity distribution of the Stokes light in the optical fiber in a length direction of the optical fiber and data on an intensity distribution of the anti-Stokes light in the optical fiber in the length direction; and a data processing unit configured to calculate a product of a value obtained by applying an FIR (Finite Impulse Response) filter to the intensity distribution of the Stokes light in the optical fiber in the length direction, and a value obtained by applying the FIR filter to the intensity distribution of the anti-Stokes light in the optical fiber in the length direction for each of locations on the optical fiber in the length direction, and to determine whether or not abnormality is present based on a result of the calculation.

According another aspect of the disclosed technique, there is provided an abnormality detection method, including: by using a Raman scattered light detection unit, acquiring an intensity distribution of Stokes light and an intensity distribution of anti-Stokes light in an optical fiber in a length direction of the optical fiber; and by using a data processing unit, calculating a product of a value obtained by applying an FIR (Finite Impulse Response) filter to the intensity distribution of the Stokes light in the optical fiber in the length direction, and a value obtained by applying the FIR filter to the intensity distribution of the anti-Stokes light in the optical fiber in the length direction for each of locations on the optical fiber in the length direction.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 21 is a table illustrating the result of calculating average losses from FIG. 19 by using a correction function F(ΔP);

FIG. 22 is a table describing a second method for calculating transmission losses;

FIG. 23 is a table illustrating the result of calculation of the amount of light at each of peaks P2 and P3;

FIG. 24 is a table illustrating the visually read average losses and the result of the calculation of the transmission losses by the second method;

DESCRIPTION OF EMBODIMENTS

Before describing an embodiment, a prelude for facilitating understanding of the embodiment will be described below.

An abnormality detection system according to the embodiment detects abnormality by utilizing the fact that the transmission loss of an optical fiber changes in response to application of bending stress.

Figure 1:
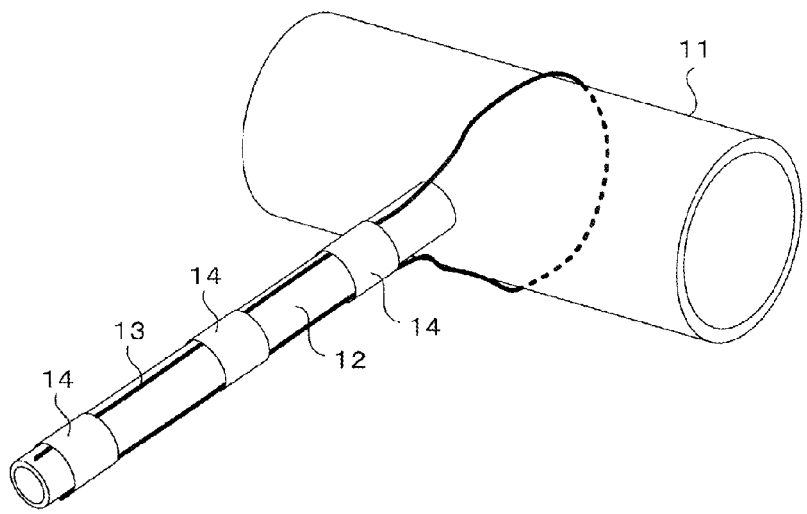
FIG. 1 is a view illustrating a state where an optical fiber is wound with a constant tension around a portion of a main pipe where a branch pipe is welded.

FIG. 1 is a view illustrating a state where an optical fiber 13 is wound with a constant tension around a portion of a main pipe 11 where a branch pipe 12 is welded. The optical fiber 13 is partly fixed to the branch pipe 12 with pieces of tape 14.

The flow of liquid or gas inside the main pipe 11 and the branch pipe 12 changes as the plant is operated and stopped. As a result, the temperature of the main pipe 11 and the branch pipe 12 changes accordingly. By this temperature change, the main pipe 11 and the branch pipe 12 expand or shrink, and the bending stress and the tensile stress applied to the optical fiber 13 change accordingly.

When the optical fiber 13 receives a bending stress or tensile stress of a certain degree or higher, the transmission loss thereof increases. It is, then, possible to determine the presence of abnormality, for example, by comparing the transmission loss in a past operating or stopped period and the current transmission loss.

Figure 2:
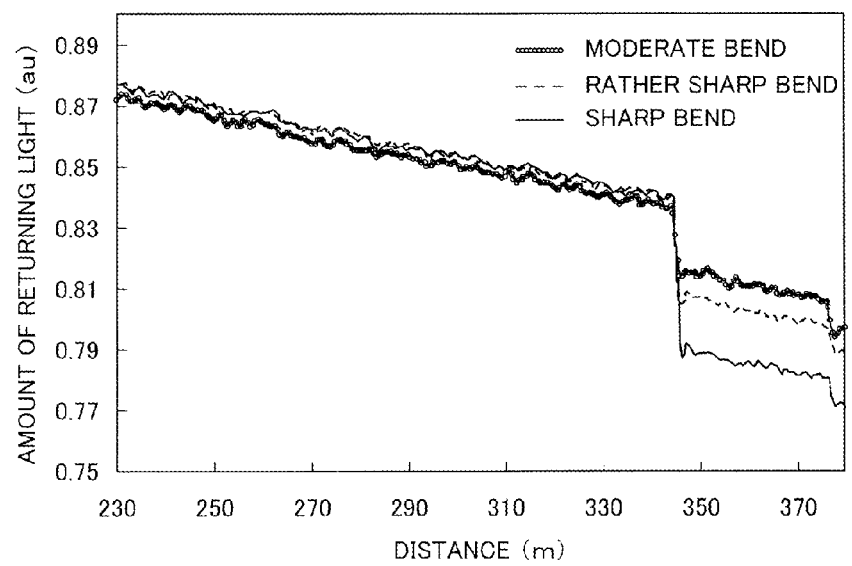
FIG. 2 is a graph illustrating the results of observation on transmission loss in a state where the optical fiber is bent moderately, transmission loss in a state where the optical fiber is bent rather sharply, and transmission loss in a state where the optical fiber is bent sharply.

FIG. 2 is a graph with the horizontal axis representing distance (location of the optical fiber in the length direction thereof) versus the vertical axis representing the intensity of returning light, illustrating the results of observation on the transmission loss in a state where the optical fiber is bent moderately, the transmission loss in a state where the optical fiber is bent rather sharply, and the transmission loss in a state where the optical fiber is bent sharply.

Figure 3:
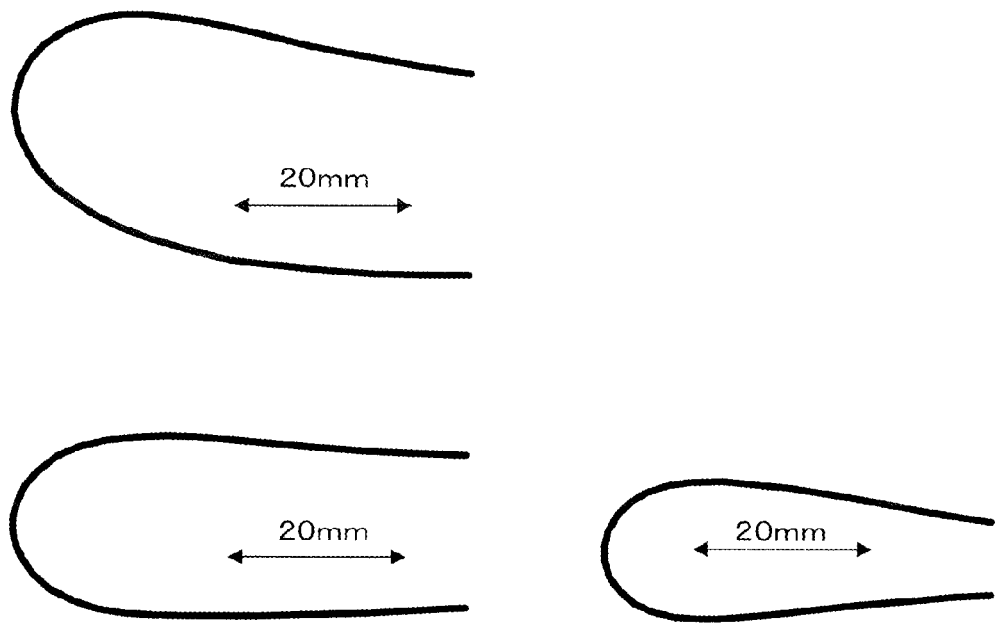
FIG. 3 is a view specifically illustrating the moderate bend, the rather sharp bend, and the sharp bend.

Note that the moderate bend refers to a bend (with a bend radius of about 10 mm) as illustrated in FIG. 3; the rather sharp bend refers to a bend slightly sharper than that of the moderate bend (see FIG. 3); and the sharp bend refers to a bend slightly sharper than that of the rather sharp bend (see FIG. 3). Moreover, in FIG. 2, the intensity of returning light is normalized based on the amount of light at a 0-m location in the optical fiber in the length direction.

FIG. 2 indicates that transmission losses occur at an approximately 340-m location in the optical fibers in the length direction in accordance with the degrees of the bends.

Assume for example that, during normal operation, an optical fiber is bent moderately and a certain amount of transmission loss occurs at a given location in the optical fiber in the length direction. In this case, it is possible to determine that some abnormality has occurred if the transmission loss of the optical fiber abruptly changes.

As indicated by FIG. 2, the intensity of returning light changes by the location in the optical fiber in the length direction. It is therefore impossible to determine the presence of abnormality simply from the intensity of returning light. Hence, in order to automatically detect abnormality, it is important to detect change in the intensity of returning light.

Patent Document 1 describes a method in which the intensity distribution of returning light is differentiated twice for the purpose of accurately measuring the location of a connected portion of optical fibers and the connection loss thereat. It is conceivable to utilize this method to detect the presence of abnormality.

Figure 4:
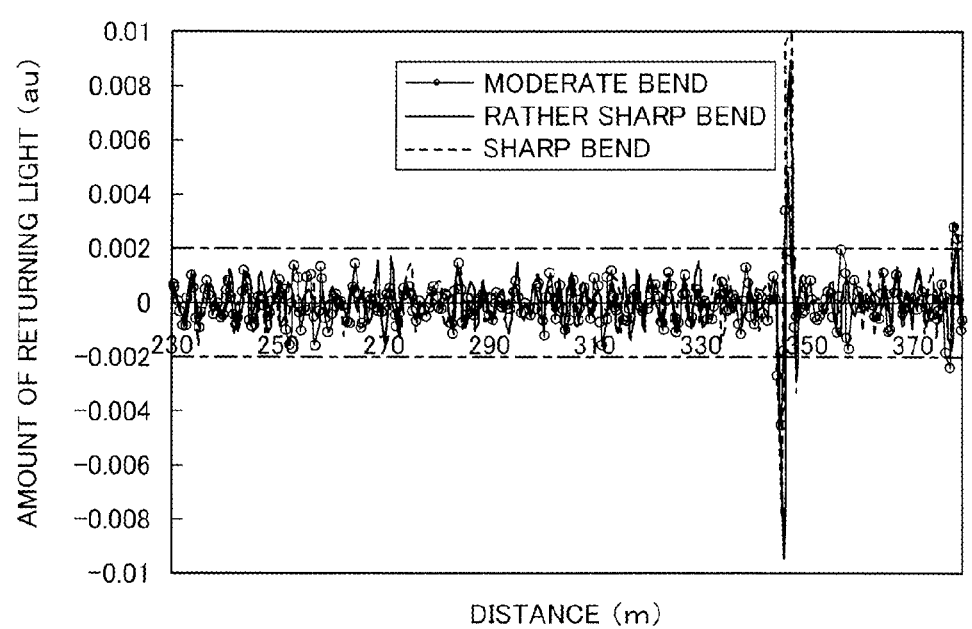
FIG. 4 is a graph illustrating the result of double differentiation on the intensity distributions of returning light illustrated in FIG. 2.

FIG. 4 is a graph illustrating the result of double differentiation on the intensity distributions of returning light illustrated in FIG. 2. The dashed lines in FIG. 4 indicate a range of 3σ (σ is the standard deviation).

As illustrated in this FIG. 4, the double differentiation on the intensity distributions of returning light heightens the changes in the intensities of the returning light. It is thus possible to relatively accurately detect the presence of a transmission loss and the location where the transmission loss has occurred.

Here, it is preferable to set a threshold to about 3σ in order to remove noise components. In the case where the threshold is set at 3σ, the reliability of the detection is not said to be high since the peak level at the moderately bent portion is slightly higher than the noise level.

FIG. 2 indicates that the difference between the amounts of returning light before and after the rather sharply bent location is approximately 2.4%. In other words, this method does not accurately detect the occurrence of abnormality unless there is a bending stress or tensile stress that changes the amount of light by at least 2.4%.

While an optical pulse detector (Optical Time Domain Reflectmeter: OTDR) used in Patent Document 1 uses Rayleigh scattered light, a similar result may be obtained by using Raman scattered light which is used by temperature distribution measurement apparatuses (DTS). By using a temperature distribution measurement apparatus, it is possible to perform temperature distribution measurement and abnormality detection at the same time.

Figure 5:
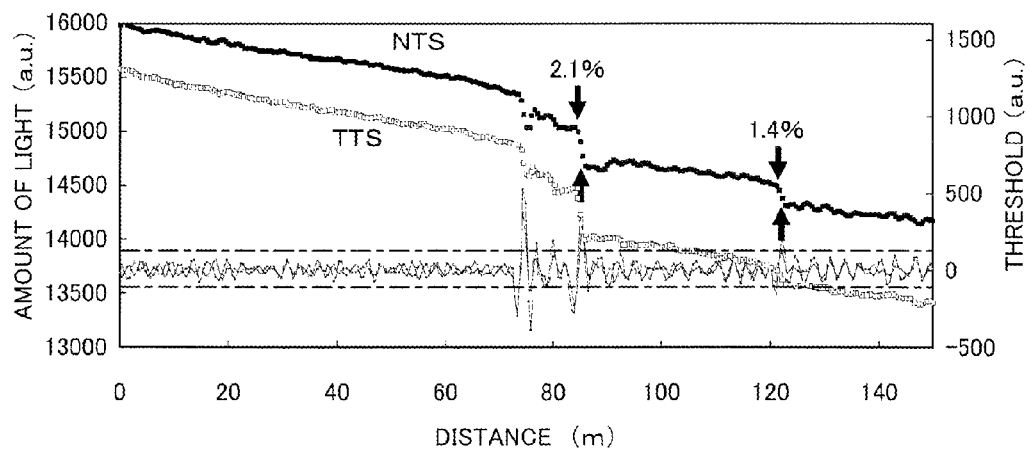
FIG. 5 is a graph illustrating the intensity distribution of Raman scattered light in a state where a bending stress is applied, together with the result of double differentiation on the intensity distribution.

FIG. 5 is a graph with the horizontal axis representing distance (location of the optical fiber in the length direction) versus the vertical axis representing the amount of returning light (left) and threshold (right), illustrating the intensity distribution of Raman scattered light in a state where a bending stress is applied, together with the result of double differentiation on the intensity distribution. Note that in FIG. 5, NTS indicates a measurement result for Stokes light while TTS indicates a measurement result for anti-Stokes light. Moreover, the dashed lines in FIG. 5 indicate a range of 3σ.

This FIG. 5 indicates that, without about a 2%-difference in the amount of light, the method involving double differentiation on returning light does not accurately detect abnormality even by using Stokes light and anti-Stokes light.

Thus, the method of detecting abnormality through double differentiation on the intensity distribution of returning light has this problem in that abnormality is not detected until the transmission loss increases to a certain extent, i.e. abnormality is not detected at an early stage. In facilities such as factories and chemical plants, it is desired to detect abnormality at an early stage because a delay in abnormality detection may worsen accidents.

Another reason for the incapability of detecting abnormality at an early stage is the influence of temperature. The intensity of Raman scattered light changes with temperature. Hence, the intensity of returning light is related to the stress applied to the optical fiber and the temperature.

Figure 6:
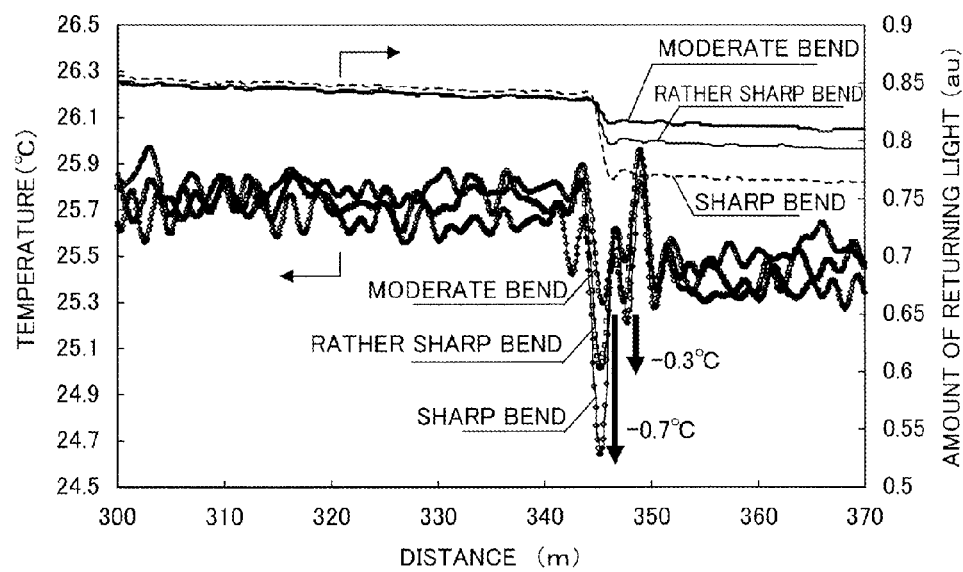
FIG. 6 is a graph illustrating the intensity distributions of returning light together with corresponding temperature distributions obtained by a temperature distribution measurement apparatus.

FIG. 6 is a graph with the horizontal axis representing distance (location of the optical fiber in the length direction) versus the vertical axis representing temperature (left) and the intensity of returning light (right), illustrating the intensity distributions of returning light together with corresponding temperature distributions obtained by a temperature distribution measurement apparatus.

Note that in FIG. 6, the intensity of returning light is normalized based on the amount of light at a 0-m location in the optical fiber in the length direction. Moreover, in this example, a bending stress is applied to an approximately 345-m location on the optical fiber in the length direction.

FIG. 6 indicates that the error in measured temperature is large when the bend radius of the optical fiber is small and the transmission loss is thus large. Note that in FIG. 6, the temperature difference between before and after the location where the bending stress is applied is not a problem since it originates from the positional difference therebetween on the path along which the optical fiber is laid.

There is a case, for example, where a housing-type data center is performing temperature monitoring by using optical fibers, and the stress applied to an optical fiber laid on a rack has changed for some reason, thereby changing the intensity of returning light and making it impossible to accurately detect the temperature. In this case, the temperature is detected to be higher than the actual temperature, or the temperature is detected to be lower than the actual temperature.

In the case where the temperature is detected to be higher than the actual temperature, abnormality is determined to be present although there is no abnormality. On the other hand, in the case where the temperature is detected to be lower than the actual temperature, no abnormality is determined to be present although the temperature is above an allowable upper limit temperature.

In the following embodiment, an abnormality detection system will be described which is capable of detecting abnormality at an early stage, the abnormality occurring in a facility such as a chemical plant, an oil refinery plant, or a thermal power plant.

Embodiment

Figure 7:
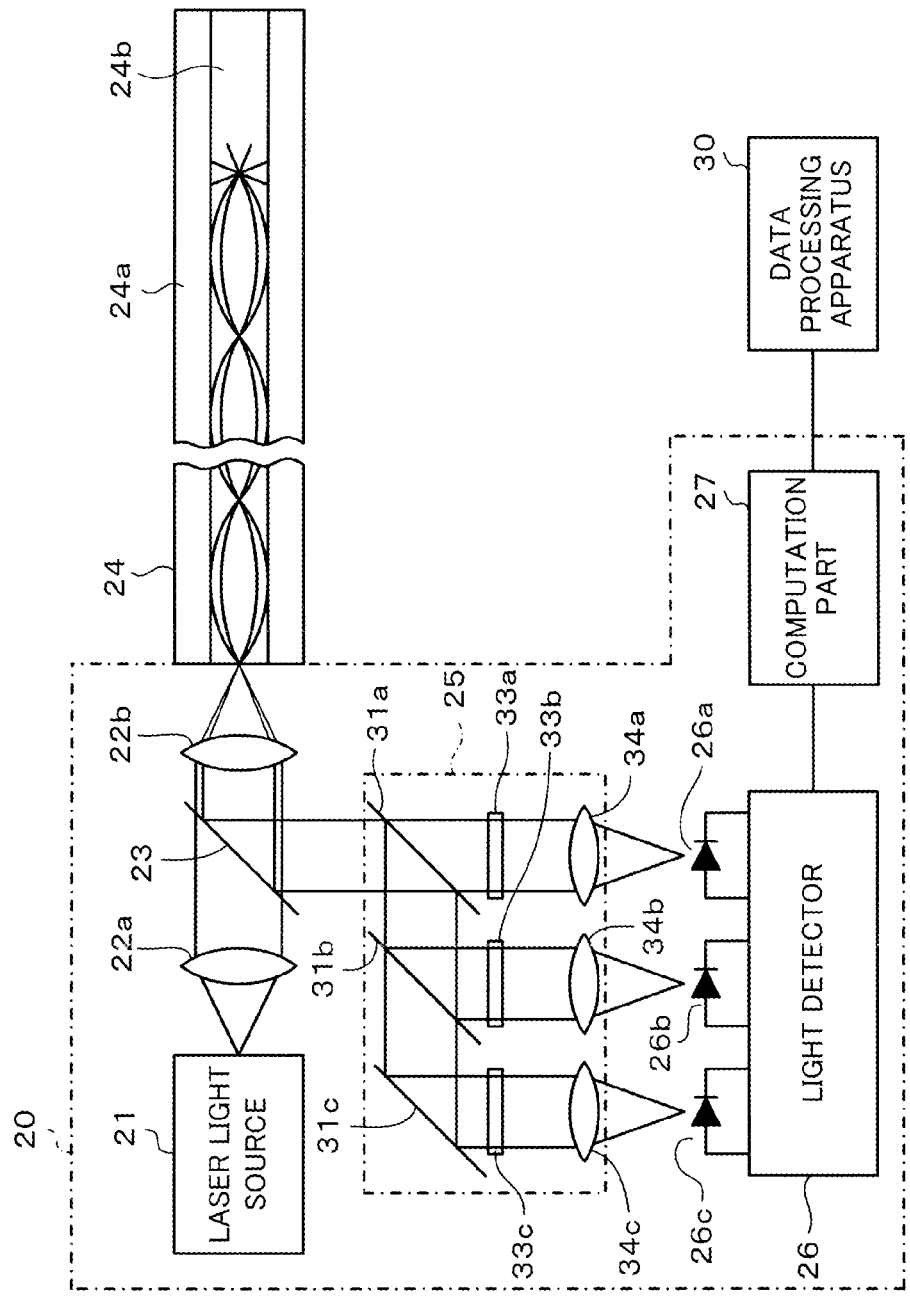
FIG. 7 is a block diagram illustrating an abnormality detection system according to an embodiment.
Figure 8:
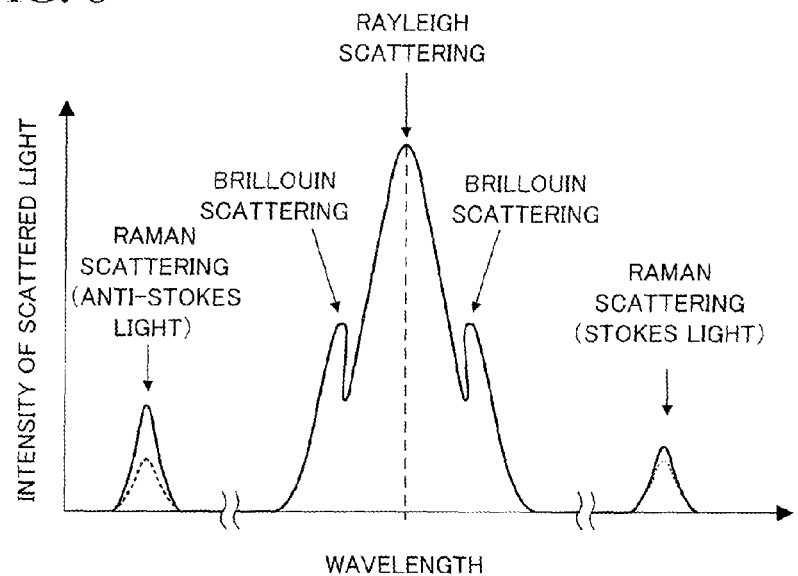
FIG. 8 is a graph illustrating the spectrum of backscattered light.
Figure 9:
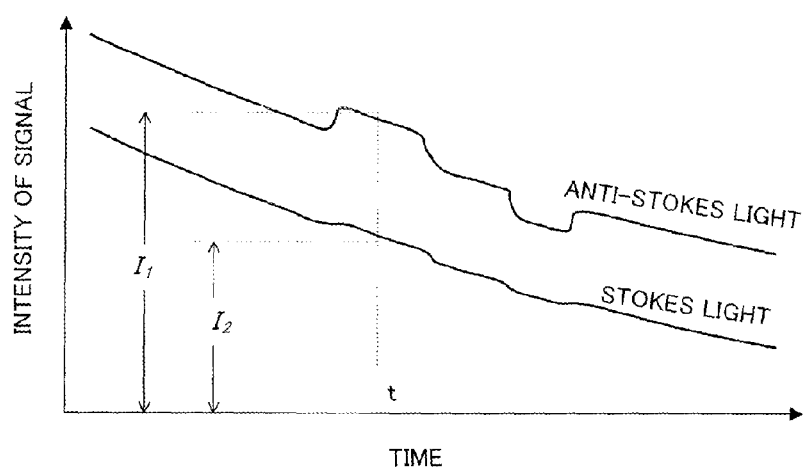
FIG. 9 is a graph illustrating the time-series intensity distribution of Raman scattered light.

FIG. 7 is a block diagram illustrating an abnormality detection system according to an embodiment. Moreover, FIG. 8 is a graph illustrating the spectrum of backscattered light, and FIG. 9 is a graph illustrating the time-series intensity distribution of Raman scattered light detected by a Raman scattered light detector.

As illustrated in FIG. 7, the abnormality detection system according to this embodiment includes a Raman scattered light detection apparatus 20 and a data processing apparatus 30 configured to process data outputted from the Raman scattered light detection apparatus 20. The Raman scattered light detection apparatus 20 is one example of a Raman scattered light detection unit, and the data processing apparatus 30 is one example of a data processing unit.

As illustrated in FIG. 7, the Raman scattered light detection apparatus 20 includes a laser light source 21, lenses 22a and 22b, a beam splitter 23, a wavelength separation part 25, a light detector 26, and a computation part 27. The Raman scattered light detection apparatus 20 is used while connected to an optical fiber 24. The optical fiber 24 is laid on the peripheries of pipes 11 and 12 and partly fixed to the pipes 11 and 12 with pieces of tape 14 or the like as in FIG. 1, for example.

The laser light source 21 is configured to output laser of a predetermined pulse width at regular intervals. This laser travels through the lens 22a, the beam splitter 23, and the lens 22b and enters the optical fiber 24 from the light source-side end of the optical fiber 24. Note that in FIG. 7, reference numeral 24a denotes the cladding of the optical fiber 24, and reference numeral 24b denotes the core of the optical fiber 24.

Part of the light having entered the optical fiber 24 is backscattered by molecules composing the optical fiber 24. As illustrated in FIG. 8, the backscattered light includes Rayleigh scattered light, Brillouin scattered light, and Raman scattered light. The Rayleigh scattered light is light of the same wavelengths as the incoming light, while the Brillouin scattered light and the Raman scattered light are light of wavelengths shifted from the incoming wavelength.

As the Raman scattered light, there are Stokes light shifted to the longer wavelength side from the incoming light, and anti-Stokes light shifted to the shorter wavelength side from the incoming light. The intensity of the Stokes light and the intensity of the anti-Stokes light both change with temperature. However, the amount of change with temperature is small for the Stokes light, while the amount of the change with temperature is large for the anti-Stokes light. In other words, it may be said that the Stokes light has low temperature dependency while the anti-Stokes light has high temperature dependency.

As illustrated in FIG. 7, this backscattered light travels backward through the optical fiber 24 and exits from the light source-side end. After that, the light passes through the lens 22b, is reflected on the beam splitter 23, and enters the wavelength separation part 25.

The wavelength separation part 25 includes beam splitters 31a to 31c configured to transmit or reflect light in accordance with its wavelength, and optical filters 33a to 33c configured to transmit light of specific wavelengths. Moreover, wavelength separation part 25 includes condensing lenses 34a to 34c configured to condense the light transmitted by the optical filters 33a to 33c, onto light receiving parts 26a to 26c of the light detector 26, respectively.

The light having entered the wavelength separation part 25 is separated into Rayleigh scattered light, Stokes light, and anti-Stokes light by the beam splitters 31a to 31c and the optical filters 33a to 33c and inputted into the light receiving parts 26a to 26c of the light detector 26, respectively. As a result, the light receiving parts 26a to 26c output signals corresponding to the intensities of the Rayleigh scattered light, the Stokes light, and the anti-Stokes light, respectively.

The computation part 27 includes a computer as its constituent component. This computation part 27 is configured to store the time-series changes in the signals outputted from the light detector 26 and also compute the ratio between the intensities of the Stokes light and the anti-Stokes light to acquire the temperature distribution in the length direction of the optical fiber 24.

The backscattered light generated inside the optical fiber 24 attenuates while traveling backward through the optical fiber 24. Then, in order to correctly evaluate the temperature at the location where the backscattering has occurred, it is important to take the attenuation of the light into consideration.

FIG. 9 is a graph with the horizontal axis representing time versus the vertical axis representing signal intensity, illustrating one example of the time-series intensity distribution of Raman scattered light. The light detector 26 detects Stokes light and anti-Stokes light during a certain period of time immediately after laser pulses enter the optical fiber 24. If the temperature is even over the entire length of the optical fiber 24, the signal intensities will decrease in time, starting from the point when the laser pulses enter the optical fiber 24. Then, the time on the horizontal axis represents the distance from the light source-side end of the optical fiber 24 to the location where the backscattering has occurred, and the decrease in the signal intensities in time indicates attenuation of the light by the optical fiber 24.

If the temperature is not even in the length direction of the optical fiber 24, e.g. if there are a high temperature portion and a low temperature portion in the length direction, the signal intensities of Stokes light and anti-Stokes light will not attenuate monotonously; instead, as illustrated in FIG. 9, peaks and valleys will appear on curves representing the time-series changes in the signal intensities. In FIG. 9, $I_1$ and $I_2$ denote the intensity of the anti-Stokes light and the intensity of the Stokes light at a given time t, respectively.

Figure 10:
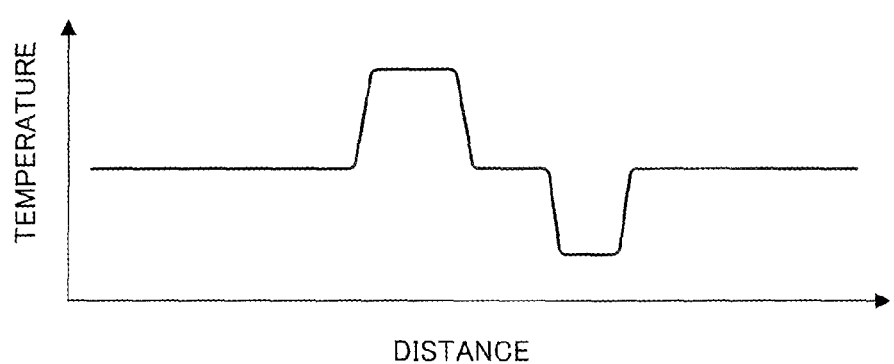
FIG. 10 is a graph illustrating a result obtained by: calculating a ratio $I_1/I_2$ at each given time based on the time-series intensity distribution of Raman scattered light in FIG. 9; and converting the horizontal axis (time) in FIG. 9 into distance and converting the vertical axis (signal intensity) in FIG. 9 into temperature.

FIG. 10 is a graph illustrating a result obtained by: calculating a ratio $I_1/I_2$ at each given time based on the time-series intensity distribution of Raman scattered light in FIG. 9; and converting the horizontal axis (time) in FIG. 9 into distance and converting the vertical axis (signal intensity) in FIG. 9 into temperature. As illustrated in this FIG. 10, the temperature distribution in the length direction of the optical fiber may be measured by calculating the ratio between the intensities of the anti-Stokes light and the Stokes light ($I_1/I_2$).

The Raman scattered light detection apparatus 20 used in this embodiment has basically the same structure as temperature distribution measurement apparatuses (DTS) and is thus capable of also measuring the temperature distribution as described above. However, the measurement of the temperature distribution may be done when needed, and is not important.

The data processing apparatus 30 includes a computer as its constituent component. Moreover, as will be described later, the data processing apparatus 30 is configured to determine the presence of abnormality by processing data outputted from the Raman scattered light detection apparatus 20, and perform a preset process such as putting out an alert if determining that abnormality is present.

By storing the path along which the optical fiber is laid (laying path in a two- or three-dimensional space) in the data processing apparatus 30, it is also possible to compute a temperature distribution in the two- or three-dimensional space from the temperature distribution in the length direction of the optical fiber 24 outputted from the Raman scattered light detection apparatus 20.

Note that the present inventors have proposed a temperature measurement method in which the temperature at a given measurement point is set as a reference, and the measured temperature values at the other measurement points are corrected using a transfer function (e.g. Patent Document 3). With this method, it is possible to accurately detect the temperature at measurement points set at intervals of 10 cm to several tens of cm in the length direction of the optical fiber.

Figure 11A:
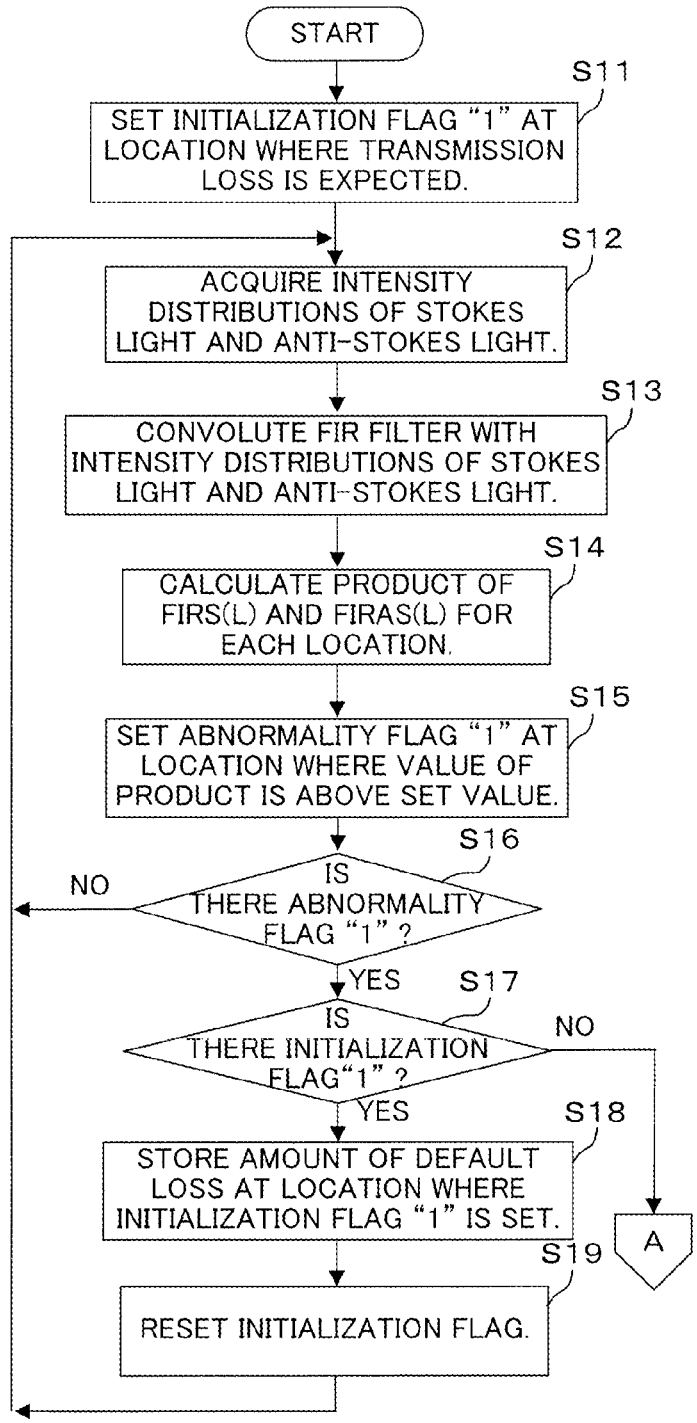
FIGS. 11A and 11B are a flowchart illustrating an abnormality detection method of the abnormality detection system according to the embodiment.
Figure 11B:
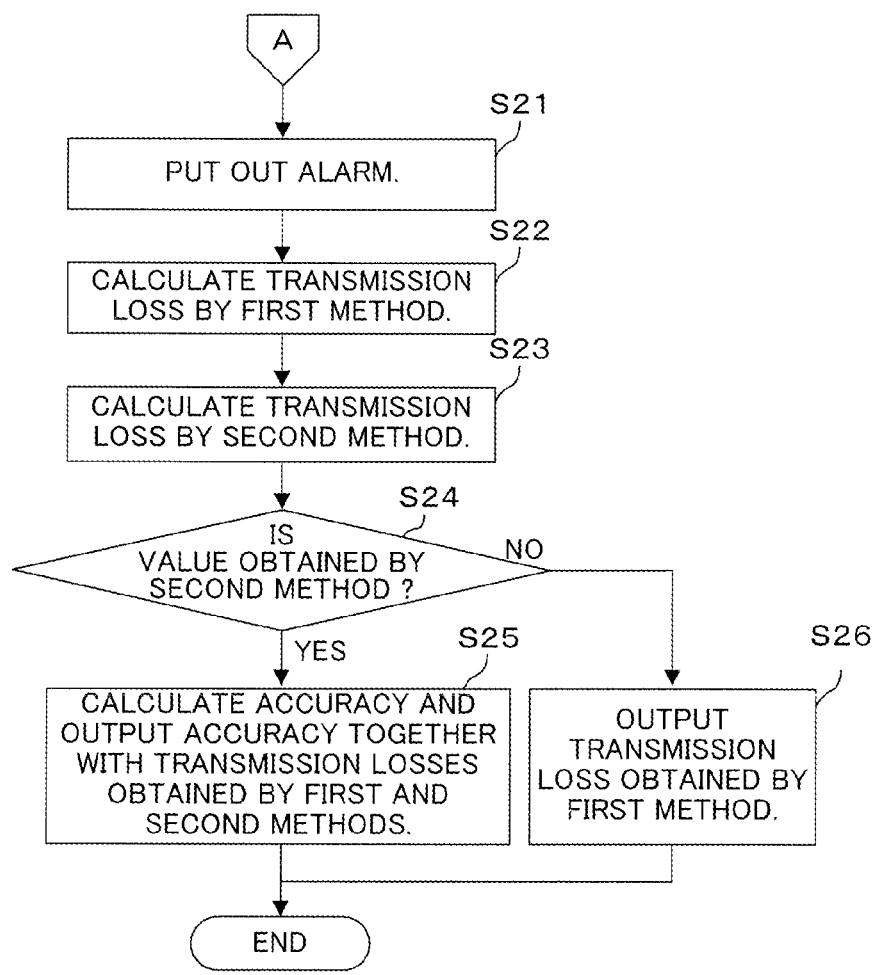

An abnormality detection method of the abnormality detection system according to this embodiment will be described below with reference to a flowchart illustrated in FIGS. 11A and 11B.

First, in step S11, an initialization flag "1" is set at a predetermined location on the optical fiber 24 in the length direction.

For example, in the case two optical fibers 24 are optically connected with a connector or by fusion, a transmission loss inevitably occurs at the connected portion. Thus, even if a transmission loss of a certain degree occurs at the connected portion, it is not a sign of abnormality. In step S11, the initialization flag "1" is set at a location where a transmission loss is expected, like the connected portion. Moreover, in the case where a stress of a certain degree is applied in advance to a particular location on the optical fiber 24, the initialization flag "1" is also set on that location.

Then, in step S12, the data processing apparatus 30 acquires data on the amounts of Stokes light (NTS) and anti-Stokes light (TTS) at each of given locations (measurement points) in the optical fiber 24 in the length direction from the Raman scattered light detection apparatus 20.

Figure 12:
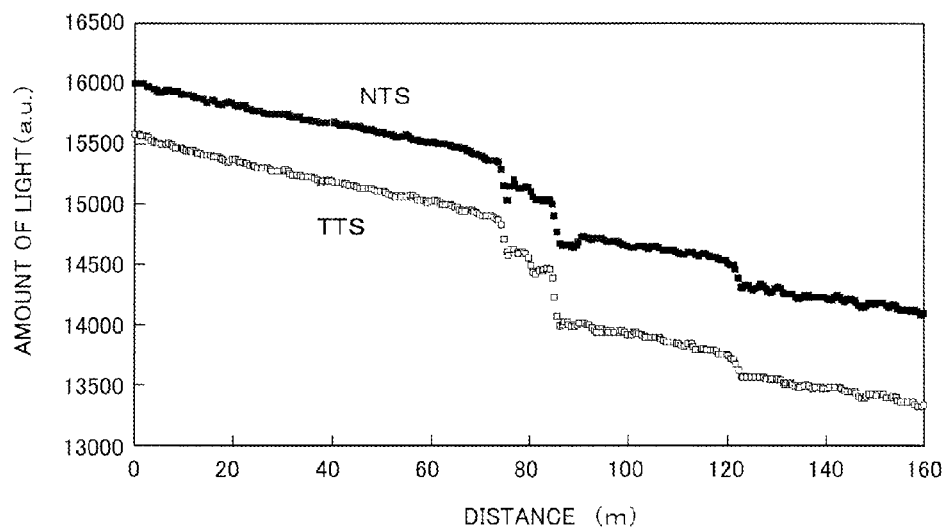
FIG. 12 is a graph illustrating data on the amounts of Stokes light (NTS) and anti-Stokes light (TTS) at each of given locations in the optical fiber in the length direction thereof.

FIG. 12 illustrates one example of the data on the amounts of the Stokes light (NTS) and the anti-Stokes light at each of the given locations in the optical fiber 24 in the length direction, i.e. the intensity distributions of the Stokes light and the anti-Stokes light.

Proceeding then to step S13, the data processing apparatus 30 applies a differential FIR (Finite Impulse Response) filter to the intensity distributions of the Stokes light and the anti-Stokes light.

Figure 13:
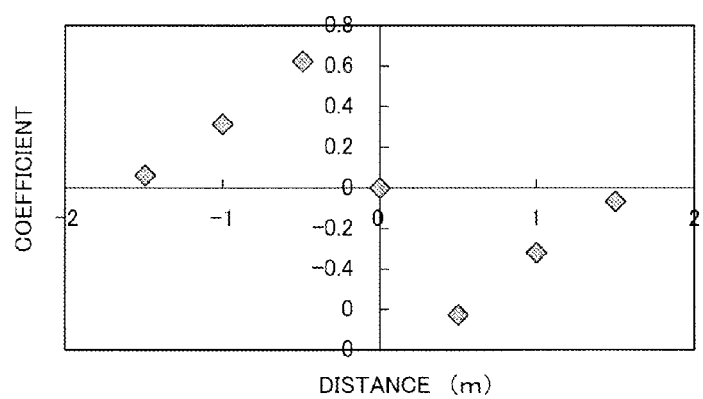
FIG. 13 is a graph illustrating one example of an FIR filter.

The differential FIR filter is a filter which has the characteristics of both a differential filter and a low-pass filter, unlike a unit-step-type differential filter. FIG. 13 illustrates one example of the FIR filter used in this embodiment.

Figure 14:
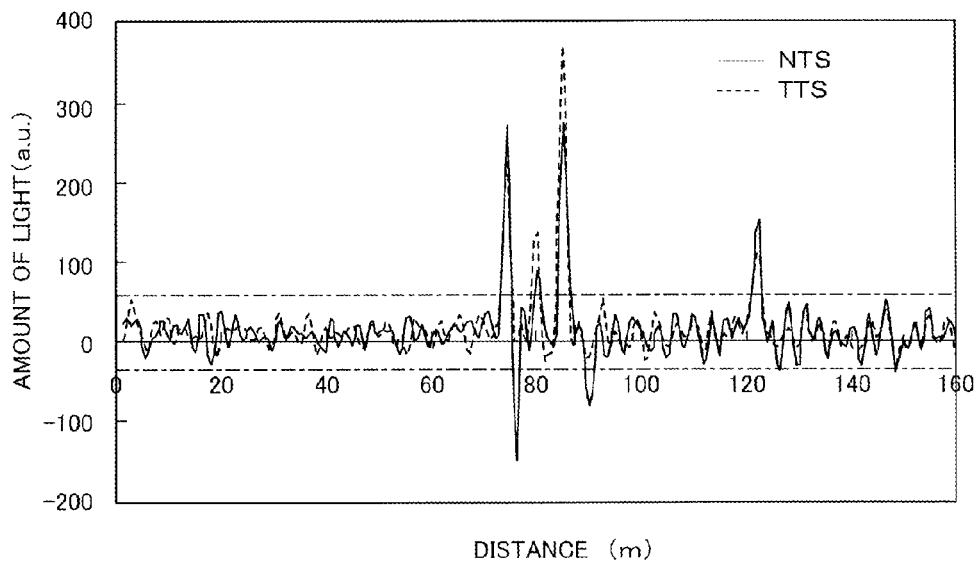
FIG. 14 is a graph illustrating the result of convoluting the FIR filter illustrated in FIG. 13 with the intensity distributions in FIG. 12.

This FIR filter is convoluted with the intensity distributions of the Stokes light and the anti-Stokes light. FIG. 14 is a graph illustrating the result of the convolution of the FIR filter illustrated in FIG. 13 with the intensity distributions in FIG. 12.

As illustrated in this FIG. 14, transmission losses are heightened by convoluting the FIR filter with the intensity distribution of the Stokes light and the intensity distribution of the anti-Stokes light.

Proceeding then to step S14, the data processing apparatus 30 calculates the product of values FIRS(L) and FIRAS (L), which are obtained by convoluting the FIR filter with the intensity distributions of the Stokes light and the anti-Stokes light, for each location L on the optical fiber 24 in the length direction.

Figure 15:
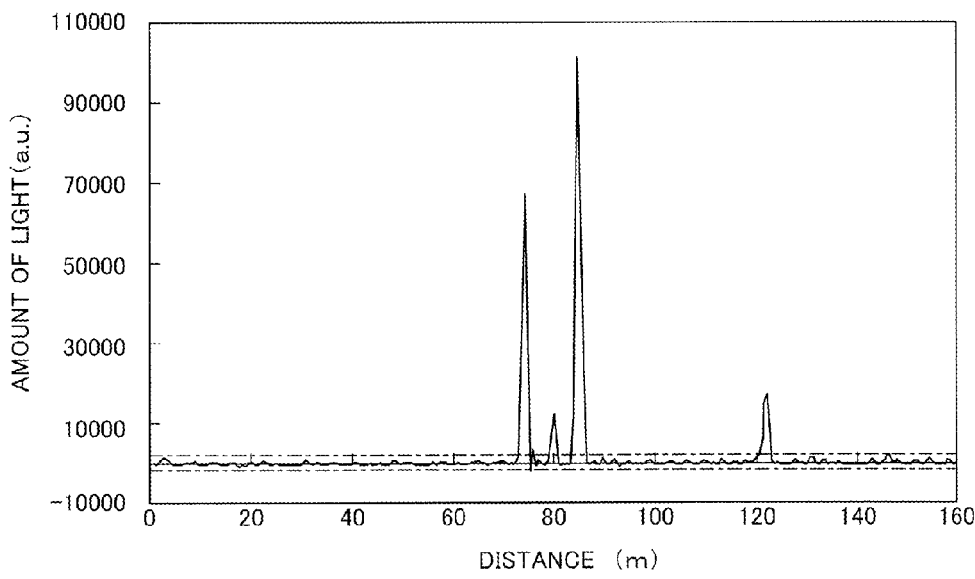
FIG. 15 is a graph illustrating the result of calculating the product of a value FIRS(L) which is obtained by convoluting the FIR filter with the intensity distribution of the Stokes light, and a value FIRAS(L) which is obtained by convoluting the FIR filter with the intensity distribution of the anti-Stokes light, for each location on the optical fiber in the length direction.

FIG. 15 is a graph illustrating the result of calculating the product of the value FIRS(L), which is obtained by convoluting the FIR filter with the intensity distribution of the Stokes light, and the value FIRAS(L), which is obtained by convoluting the FIR filter with the intensity distribution of the anti-Stokes light, for each location on the optical fiber in the length direction.

As is clear from this FIG. 15, the computation of the product of the value FIRS(L) and the value FIRAS(L) reduces the noise components and hence further heightens the transmission losses.

Proceeding then to step S15, the data processing apparatus 30 compares the value of the product of the value FIRS(L) and the value FIRAS(L) with a set value for each location L. If the value of the product of the value FIRS(L) and the value FIRAS(L) is greater than the set value, the data processing apparatus 30 determines that abnormality is present, and sets an abnormality flag "1" at that location L.

The set value may be set to about 3σ, for example. Note that, in the case where a later-described default loss is registered at the location L, the set value is set to (default loss+error range).

Note that a transmission loss above the set value occurs at each of the portions where the initialization flag "1" is set in step S11, i.e. the connected portion of the optical fibers and the portion thereof where a stress of a certain degree is applied in advance. Thus, in the first loop, the abnormality flag "1" is set at each of these portions.

Proceeding then to step S16, the data processing apparatus 30 determines whether or not there is any location where the abnormality flag "1" is set. The data processing apparatus 30 proceeds to step S17 if determining that there is a location where the abnormality flag "1" is set. The data processing apparatus 30 returns to step S12 and continues the process if determining that there is no location where the abnormality flag "1" is set.

If proceeding to step S17 from step S16, the data processing apparatus 30 determines whether or not the initialization flag "1" is set at the location where the abnormality flag "1" is set. The data processing apparatus 30 proceeds to step S18 if determining that the initialization flag "1" is set at the location where the abnormality flag "1" is set. The data processing apparatus 30 proceeds to step S21 if determining that the initialization flag "1" is not set.

If proceeding to step S18 from step S17, the data processing apparatus 30 registers the value FIRS(L) and the value FIRAS(L) at the location L where the initialization flag "1" is set, as a default loss and stores it in the data processing apparatus 30.

Proceeding then to step S19, the data processing apparatus 30 resets the initialization flag "1". Thereafter, the data processing apparatus 30 returns to step S12 and repeats the process described above.

In the second and subsequent loops, the initialization flags have already been reset. Hence, if there is any location where the abnormality flag "1" is set in step S15, the data processing apparatus 30 proceeds to step S21 from step S17.

Once proceeding to step S21, the data processing apparatus 30 notifies the presence of abnormality by putting out an alert, for example. Proceeding then to step S22, the data processing apparatus 30 performs a calculation to quantify the amount of loss by using a first method.

In the first method, data is normalized, and the amount of loss (dB) is found from the height of the corresponding peak from a baseline based on a configuration table. The data processing apparatus 30 calculates the amount of loss from the method described below, for example.

First, the data processing apparatus 30 normalizes an abnormality detection signal P(L) from the equation (1) given below.

$$P(L)=FIRS(L) \cdot FIRAS(L) \div \sqrt{FIRS(L)^2 + FIRAS(L)^2} \qquad (1)$$

Note that P(L) may be one with the absolute value of the left-hand side of the equation (1).

Figure 16:
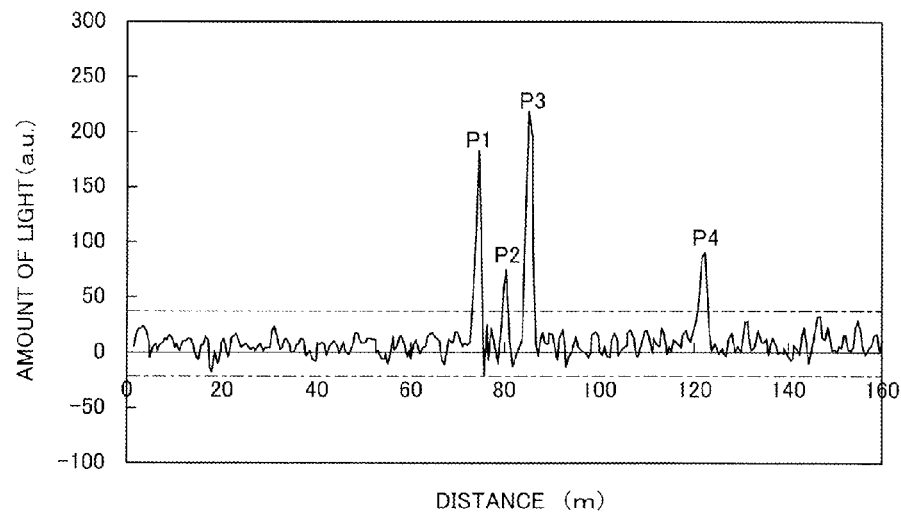
FIG. 16 is a graph illustrating an abnormality detection signal which is normalized.

FIG. 16 is a graph illustrating the abnormality detection signal P(L) thus normalized. In FIG. 16, peaks appear at the locations where abnormality is detected. These peak locations are named as Lalert. In FIG. 16, P1, P2, P3, and P4 are set as the peak locations Lalert.

Then, Pave is set as the average of the values of P(L) excluding the peak locations and locations therearound. Note that Pave may be the average of the entire P(L).

Thereafter, a peak height $\Delta P$ is calculated from the equation (2) given below.

$$\Delta P = P(\text{Lalert}) - P\text{ave} \qquad (2)$$

A transmission loss Loss1(L) is calculated from the equation (3) given below with $F(\Delta P)$ as a correction function.

$$\text{Loss1}(L) = -10 \cdot \log(1 - F(\Delta P)) \qquad (3)$$

Once the amount of loss Loss1(L) is found by the first method as described above, the data processing apparatus 30 proceeds to step S23. Then, in step S23, the data processing apparatus 30 attempts to quantify the amount of loss by using a second method.

The second method is under the assumption that a loss spot of interest has other loss spots present on both sides thereof. The other loss spots may each be the location of a neighboring peak or a location where a default loss is registered like the connected portion of optical fibers. Then, the values of the spots before and after the location where abnormality is detected are linearly approximated by the least-median-of-squares (LMedS) method or the like, and the loss (dB) is found from the difference between these segments.

In this case, too, like the first method, an abnormality detection signal P(L) is calculated from the equation (4) given below.

$$P(L)=FIRS(L) \cdot FIRAS(L) \div \sqrt{FIRS(L)^2 + FIRAS(L)^2} \qquad (4)$$

As illustrated in FIG. 16, peaks appear on a graph of the normalized abnormality detection signal at the locations where abnormality is detected. These peak locations are named as Lalert. Moreover, Pave is set as the average of the values of P(L) excluding the peak locations and portions therearound (or the average of the entire P(L)). Then, a peak height $\Delta P$ is calculated from the equation (5) given below.

$$\Delta P = P(\text{Lalert}) - P\text{ave} \qquad (5)$$

Thereafter, locations LF and LR of both ends of the full width at half maximum of each peak are found.

Figure 17:
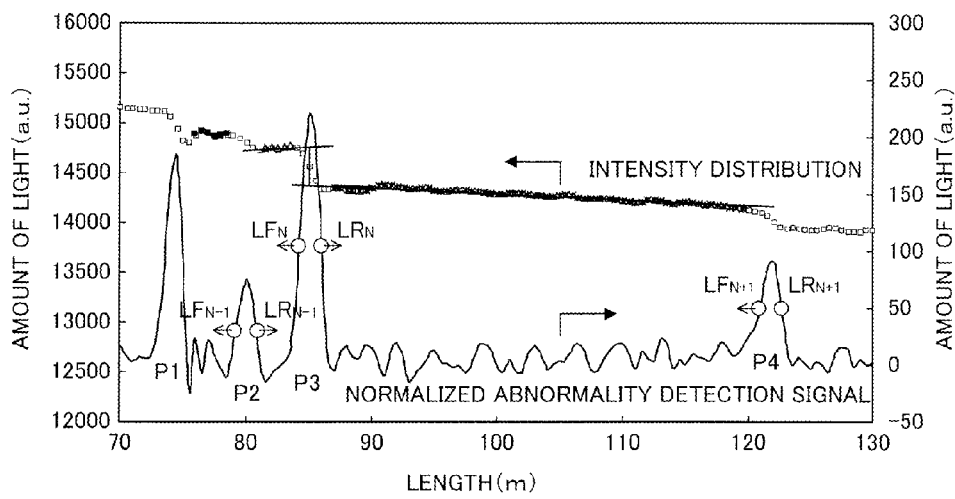
FIG. 17 is a graph illustrating an intensity distribution obtained by averaging the Stokes light and the anti-Stokes light, together with the normalized abnormality detection signal.

FIG. 17 is a graph illustrating an intensity distribution obtained by averaging the Stokes light and the anti-Stokes light, together with the normalized abnormality detection signal.

Assume, for example, that as illustrated in FIG. 17, the locations LF and LR of both ends of the full width at half maximum of a peak of interest (P3 in FIG. 17) are $LF_N$ and $LR_N$, respectively, the two locations at both ends of the full width at half maximum of the next peak on the light source side are $LF_{N-1}$ and $LR_{N-1}$, respectively, and the two locations at both ends of the full width at half maximum of the peak on the opposite side are $LF_{N+1}$ and $LR_{N+1}$, respectively. Then, an amount S(L) of the Stokes light and an amount AS(L) of the anti-Stokes light between $LR_{N-1}$ and $LF_N$ are linearly approximated, and the amount S(L) of the Stokes light and the amount AS(L) of the anti-Stokes light between $LR_N$ and $LF_{N+1}$ are linearly approximated.

The values of the four straight lines thus obtained at the location L (=Lalert) are set as PS1(Lalert), PS2(Lalert), PAS1(Lalert), and PAS2(Lalert), respectively. In this case, the difference between the PS1(Lalert) and PS2(Lalert) at the location Lalert is expressed by the equation (6) given below, and the difference between the PAS1(Lalert) and PAS2(Lalert) at the location Lalert is expressed by the equation (7) given below.

$$\Delta PS(\text{Lalert}) = \text{abs}(PS1(\text{Lalert}) - PS2(\text{Lalert})) \quad (6)$$

$$\Delta PAS(\text{Lalert}) = \text{abs}(PAS1(\text{Lalert}) - PAS2(\text{Lalert})) \quad (7)$$

These values are used in the equation (8) given below to calculate a transmission loss Loss2(L).

$$\text{Loss2}(\text{Lalert}) = -10 \cdot \log(1 - 2(\Delta PS(\text{Lalert}) + \Delta PAS(\text{Lalert})) \div (PS1(\text{Lalert}) + PS2(\text{Lalert}) + PAS1(\text{Lalert}) + PAS2(\text{Lalert}))) \quad (8)$$

$LF_N$ and $LP_N$ may be set to locations slightly farther away from the center of the peak than are the locations illustrated in FIG. 17. This is because, in general, the amount of light in a situation where a loss has occurred exhibits kink characteristics, and the residuals from the approximated linear data may be reduced by excluding regions indicating such kink characteristics.

Proceeding then to step S24, the data processing apparatus 30 determines whether or not the transmission loss Loss2(L) is obtained by the second method. The data processing apparatus 30 proceeds to step S25 if the transmission loss Loss2(L) is obtained by the second method. In step S25, the data processing apparatus 30 compares the transmission loss Loss1(L) obtained by the first method and the transmission loss Loss2(L) obtained by the second method and calculates accuracy A(%) from the equation (9) given below.

$$A = 10^B \times 100 \quad (9)$$

Here, B=(−abs (Loss1(L)−Loss2(L))÷10). Also, the unit of the transmission loss Loss1(L) and the transmission loss Loss2(L) is dB.

Figures 18, 19, 20:
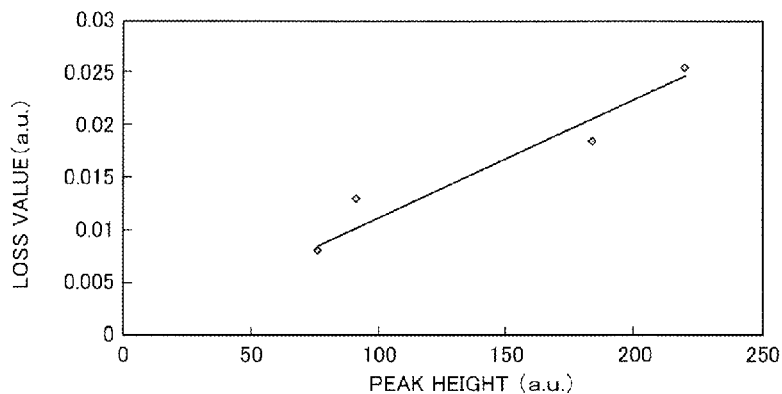
FIG. 18 is a table illustrating an example of the display of transmission loss.
FIG. 19 is a table illustrating average losses visually read from the intensity distribution of returning light illustrated in FIG. 12, and peak values read from FIG. 16.
FIG. 20 is a graph illustrating the relationship between the peak values and the average losses illustrated in FIG. 19.

Then, the data processing apparatus 30 displays each location where abnormality has occurred, the average of the transmission loss Loss1(L) and the transmission loss Loss2 (L), and the accuracy A on a display, for example. FIG. 18 illustrates an example of such display of the transmission losses.

On the other hand, if, of the two methods, the transmission loss Loss2(L) by the second method is not obtained, the data processing apparatus 30 proceeds to step S26 from step S24. Then, the data processing apparatus 30 displays each location where abnormality has occurred and the transmission loss Loss1(L) on a display, for example.

The abnormality detection system according to this embodiment may accurately detect subtle changes in the stress applied to the optical fiber. Therefore, it is possible to detect the occurrence of abnormality in a facility such as a chemical plant, an oil refinery plant, or a thermal power plant at an early stage, and thus prevent an accident from occurring or worsening.

(Discussion)

FIG. 12 illustrates the intensity distributions of Stokes light and anti-Stokes light in an optical fiber laid along a given laying path. In the above embodiment, a so-called single end-type light detection apparatus is used to which one end of an optical fiber is connected. Alternatively, a so-called loop-type light detection apparatus may be used to which both ends of an optical fiber are connected.

In the case of using a loop-type light detection apparatus, an intensity distribution may be obtained when laser is applied to one end side and returning light is detected, and also when laser is applied to the other end side and returning light is detected. Transmission losses may be calculated by using these intensity distributions. In the case of displaying these transmission losses on a display or the like, both of the transmission losses may be displayed or the average thereof may be displayed.

FIG. 14 is a graph obtained by convoluting the FIR filter in FIG. 13 with the intensity distributions in FIG. 12. The convolution of the FIR filter in FIG. 13 with the intensity distributions in FIG. 12 heightens the difference between the amounts of light before and after each spot to which a stress is applied. However, in this FIG. 14, in the case where the threshold is 3σ, there are ranges in which abnormality is detected with Stokes light but the abnormality is not detected with anti-Stokes light.

FIG. 15 illustrates the result of calculating the product of the value FIRS(L) and the value FIRAS(L) for each of given locations on the optical fiber in the length direction. The phase of the noise component of the Stokes light and the phase of the noise component of the anti-Stokes light are not necessarily the same. Then, by calculating the product of the value FIRS(L) and the value FIRAS(L) for each location on the optical fiber in the length direction, the noise components are reduced, thereby further heightening the difference between the amounts of light before and after each spot to which the stress is applied.

With this FIG. 15, the locations where a transmission loss has occurred may be located with high accuracy.

FIG. 16 is the result of the normalization of the graph in FIG. 15 by the first method described above. The range of the vertical axis in FIG. 16 differs from that in FIG. 15. In FIG. 16, the noise level is relatively high, yet the peaks may be detected stably as compared to FIGS. 14 and 15.

FIG. 15 may be used in the case of locating the locations where a transmission loss has occurred. However, it is preferable to normalize the abnormality detection signal as illustrated in FIG. 16 for quantification of the transmission loss.

FIG. 19 illustrates average losses (ratios) visually read from the intensity distribution of returning light illustrated in FIG. 12, and peak values read from FIG. 16.

For instance, in the example illustrated in FIG. 5, it is possible to detect the transmission loss occurring at the 85-m location (corresponding to the peak P3 in FIG. 19), but it is impossible to detect the transmission loss occurring at the 80-m location (corresponding to the peak P2 in FIG. 19). On the other hand, with the method of the embodiment, it is possible to detect the transmission loss (the peak P2) occurring at the 80-m location, as illustrated in FIG. 19.

The average loss at the peak P2 is 0.008095, and the average loss at the peak P3 is 0.025518. Thus, with the method of the embodiment, it is possible to achieve a detection accuracy 2.5 or more times higher than that in the case of detecting abnormality spots visually from the intensity distribution of returning light in FIG. 5.

FIG. 20 is a graph illustrating the relationship between the peak values and the average losses illustrated in FIG. 19. From this FIG. 20, the correction function F (ΔP) may be defined as the equation (10) given below.

$$F(\Delta P)=1.127019\times10^{-4}\cdot\Delta P \qquad (10)$$

FIG. 21 illustrates the result of calculating transmission losses (unit: dB) from FIG. 19 by using this correction function F(ΔP). The average losses (dB) are values visually read and converted into the unit of dB, and the peak values (dB) are values obtained by the method of this embodiment. In this FIG. 21, no large difference is found between the transmission losses obtained from the peak values by using the method disclosed in this embodiment and the average losses read visually from the intensity distribution of returning light. This demonstrates that the transmission losses found by the method disclosed in the embodiment are reliable.

The second method described above will be described below in greater detail.

Assume, for example, that locations situated outward of the peak center by 1 m are employed as LF and LR, respectively. FIG. 22 illustrates the locations of the full width at half maximum (the location of the left half of the full width at half maximum and the location of the right half of the full width at half maximum) of each of the peaks P1 to P4 in the length direction of the optical fiber and the locations LF and LR.

Here, focusing on the peak P2, each of a portion to the left of LF, a portion to the right of LR, and a portion between LF and LR is linearly approximated by the least squares method, the least-median-of-squares (LMedS) method, or the like. Then, the amounts of light at the locations LF, P2, and LR are determined. Similarly, focusing on the peak P3, each of a portion to the left of LF, a portion to the right of LR, and a portion between LF and LR is linearly approximated by the least squares method, the least-median-of-squares (LMedS) method, or the like, and the amounts of light at the locations LF, P2, and LR are determined.

FIG. 23 illustrates the result of finding the amounts of light at the peaks P2 and P3 as described above. FIG. 24 illustrates the result of finding transmission losses (losses by linear approximation) at the locations of the peaks P2 and P3 from this FIG. 23. Moreover, FIG. 24 illustrates the visually read average losses (see FIG. 21) as well.

As is clear from this FIG. 24, the visually read average losses and the transmission losses obtained by the second method substantially coincide with each other.

The applicability of the technique disclosed above will be described below.

(Applicability 1)

Figure 25:
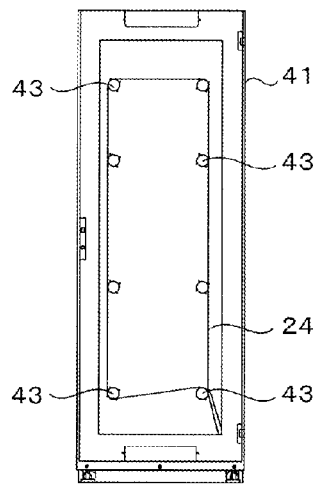
FIG. 25 is a view illustrating applicability 1.

FIG. 25 illustrates an example of application to a system configured to detect abnormality in how an optical fiber is laid on a server rack of a data center to manage air conditioning.

When a server rack 41 is newly installed in a data center, an optical fiber 24 is drawn out from an optical fiber cassette (not illustrated) placed under the floor, and the optical fiber 24 is laid on the server rack 41 with jigs 43.

Even if the operator thinks that he or she properly laid the optical fiber 24, the optical fiber 24 may be wound improperly on some of the jigs 43, thereby causing decrease in transmission loss. The decrease in transmission loss leads not only to the problem of decrease in temperature detection accuracy as described above but also to decrease in the life of the optical fiber 24.

By using the technique disclosed in the embodiment, however, the decrease in transmission loss due to the improper winding on the jigs 43 may be detected in real time. Such information is notified to the manager, and the manager notifies the improperly laid locations and a correcting instruction to the operator. In this way, the optical fiber 24 may be properly re-laid.

(Applicability 2)

FIGS. 26A to 26D illustrate an example where the abnormality detection system described in the embodiment is applied to the detection of abnormality at a connected portion of pipes as illustrated in FIG. 1.

Figure 26A:
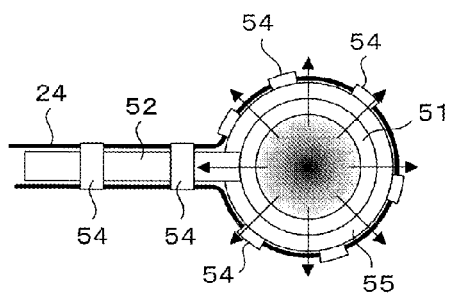
FIGS. 26A to 26D are views illustrating applicability 2.

Assume that while a plant is operated, high-temperature liquid or gas flows inside a main pipe 51, as illustrated in FIG. 26A. In this case, the pipe 51 expands when the plant is operated, and the pipe 51 shrinks when the plant is stopped. The amount of transmission loss in the optical fiber 24 when the plant is operated and the amount of transmission loss when the plant is stopped are stored in advance in the data processing apparatus 30.

Note that in FIGS. 26A to 26D, reference numeral 54 denotes pieces of tape fixing the optical fiber 24, and reference numeral 55 denotes a heat insulation material and a protection pipe disposed around the main pipe 51.

Figure 26B:
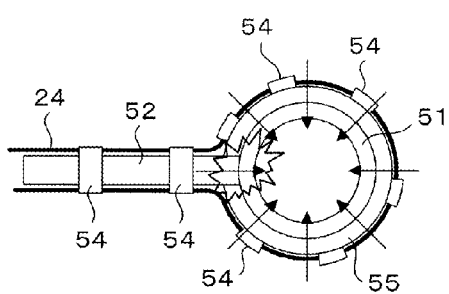
Figure 26C:
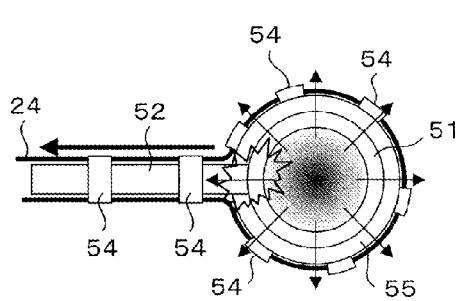
Figure 26D:
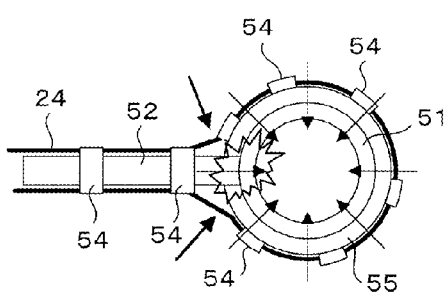

Metal fatigue occurs at a welded portion of the main pipe 51 and a branch pipe 52 as illustrated in FIG. 26B when the plant is stopped, for example. In this case, the next time the plant is run, the branch pipe 52 is pushed farther outwardly than usual as illustrated in FIG. 26C. When the plant then shifts to the stopped state, the branch pipe 52 thus pushed does not fully return as illustrated in FIG. 26D, thereby pulling the optical fiber 24. As a result, the abnormality detection system detects the abnormality.

By detecting abnormality at a connected portion of pipes in a plant or the like as described above, a serious accident is prevented from occurring.

(Applicability 3)

Figure 27:
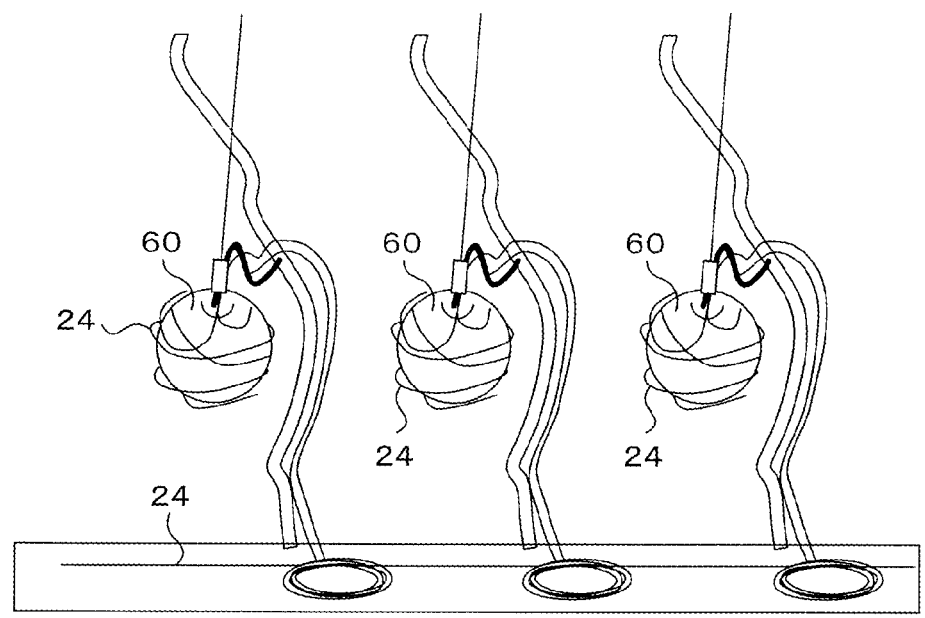
FIG. 27 is a view illustrating applicability 3.

FIG. 27 illustrates an example where the abnormality detection system described in the embodiment is applied to the growing of expensive fruits in a greenhouse and to the protection against theft thereof.

In this example, assume that, for the growing of Crown Melon in a greenhouse, a temperature distribution measurement apparatus (DTS) is used to measure the temperature of the soil, the temperature of the ambient air, and the temperature of the fruit, and the temperature of the inside of the greenhouse is managed based on these measurement results. Moreover, in this example, assume that the temperature distribution measurement apparatus is used also as the Raman scattered light detection apparatus 20 in FIG. 7, and is connected to the data processing apparatus 30 to be used for abnormality detection as well.

When a thief steals a melon 60, for example, the thief tries to unwind an optical fiber 24 wound around the melon 60. By acting carefully, the thief may avoid cutting the optical fiber 24. However, a subtle transmission loss inevitably occurs when the thief tries to unwind the optical fiber 24. Thus, the abnormality detection system may detect the abnormality.

Upon detection of the abnormality, the abnormality detection system turns on an alarm lamp or actuates an alarm buzzer as well as notifies the occurrence of the abnormality to the manager. In this way, it is possible to prevent immense damage.

All examples and conditional language recited herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An abnormality detection system comprising:
   an optical fiber;
   a Raman scattered light detector that
      is connected to one end of the optical fiber,
      detects Stokes light and anti-Stokes light at the one end of the optical fiber, which are generated in the optical fiber, and
      outputs data on an intensity distribution of the Stokes light in the optical fiber in a length direction of the optical fiber and data on an intensity distribution of the anti-Stokes light in the optical fiber in the length direction; and
   a data processor that
      calculates, for locations on the optical fiber in the length direction, a product of a value obtained by applying an FIR (Finite Impulse Response) filter to the intensity distribution of the Stokes light in the optical fiber in the length direction, and a value obtained by applying the FIR filter to the intensity distribution of the anti-Stokes light in the optical fiber in the length direction, and
      determines whether or not an abnormality is present at the locations on the optical fiber based on a result of the calculation.

2. The abnormality detection system according to claim 1, wherein the FIR filter has characteristics of both a differential filter and a low-pass filter.

3. The abnormality detection system according to claim 1, wherein
   the data processor
      normalizes the product of the value obtained by applying the FIR filter to the intensity distribution of the Stokes light and the value obtained by applying the FIR filter to the intensity distribution of the anti-Stokes light, and
      calculates a location, among the location on the optical fiber, at which abnormality has occurred and a transmission loss at the location from a peak obtained by the normalization.

4. The abnormality detection system according to claim 3, wherein
   the data processor performs the normalization by using $FIRS(L) \cdot FIRAS(L) \div sqrt(FIRS(L)^2 + FIRAS(L)^2)$,
   where $FIRS(L)$ is a value of the intensity distribution of the Stokes light after the application of the FIR filter, at a location L in the optical fiber in the length direction, and $FIRAS(L)$ is a value of the intensity distribution of the anti-Stokes light after the application of the FIR filter, at the location L in the optical fiber in the length direction.

5. The abnormality detection system according to claim 4, wherein
   the transmission loss is capable of being expressed with a function $F(\Delta P)$, where $\Delta P$ is a height of the peak after the normalization, and
   the data processor calculates a transmission loss $Loss1(L)$ at the peak location L in decibel by using $Loss1(L) = -10 \cdot \log(1 - F(\Delta P))$.

6. The abnormality detection system according to claim 3, wherein
   the data processor
      linearly approximates each of portions of the intensity distribution of the Stokes light before and after the peak and each of portions of the intensity distribution of the anti-Stokes light before and after the peak to calculate an amount of change in the Stokes light and an amount of change in the anti-Stokes light at the peak location, and
      calculates the transmission loss from a result of the calculation.

7. The abnormality detection system according to claim 1, wherein the Raman scattered light detector acquires a temperature distribution in the length direction of the optical fiber from the Stokes light and the anti-Stokes light.

8. The abnormality detection system according to claim 1, wherein the optical fiber is laid along a pipe.

9. The abnormality detection system according to claim 1, wherein the optical fiber is laid on electronic equipment.

10. The abnormality detection system according to claim 1, wherein the optical fiber is laid around a plant.

11. An abnormality detection method comprising:
    connecting a Raman scatter light detector to one end of an optical fiber;
    by using the Raman scattered light detector,
       detecting Stokes light and anti-Stokes light at the one end of the optical fiber, which are generated in the optical fiber, and
       acquiring an intensity distribution of the Stokes light and an intensity distribution of the anti-Stokes light in an optical fiber in a length direction of the optical fiber; and
    by using a data processor,
       calculating, for locations on the optical fiber in the length direction, a product of a value obtained by applying an FIR (Finite Impulse Response) filter to the intensity distribution of the Stokes light in the optical fiber in the length direction, and a value obtained by applying the FIR filter to the intensity distribution of the anti-Stokes light in the optical fiber in the length direction, and
       determining whether or not an abnormality is present at the locations on the optical fiber in the length direction based on the calculated product for the locations on the optical fiber in the length direction.

12. The abnormality detection method according to claim 11, wherein the FIR filter has characteristics of both a differential filter and a low-pass filter.

13. The abnormality detection method according to claim 11, wherein the data processor
    normalizes the product of the value obtained by applying the FIR filter to the intensity distribution of the Stokes light and the value obtained by applying the FIR filter to the intensity distribution of the anti-Stokes light, and
    calculates a location, among the location on the optical fiber, at which abnormality has occurred and a transmission loss at the location from a peak obtained by the normalization.

14. The abnormality detection method according to claim 13, wherein the data processor performs the normalization by using FIRS(L)·FIRAS(L)÷sqrt(FIRS(L)$^2$+FIRAS(L)$^2$),
where FIRS(L) is a value of the intensity distribution of the Stokes light after the application of the FIR filter, at a location L in the optical fiber in the length direction, and FIRAS(L) is a value of the intensity distribution of the anti-Stokes light after the application of the FIR filter, at the location L in the optical fiber in the length direction.

15. The abnormality detection method according to claim 14, wherein
the transmission loss is capable of being expressed with a function F(ΔP), where ΔP is a height of the peak after the normalization, and
the data processor calculates a transmission loss Loss1(L) at the peak location L in decibel by using Loss1(L)=−10·log(1−F(ΔP)).

16. The abnormality detection method according to claim 13, wherein the data processor
linearly approximates each of portions of the intensity distribution of the Stokes light before and after the peak and each of portions of the intensity distribution of the anti-Stokes light before and after the peak to calculate an amount of change in the Stokes light and an amount of change in the anti-Stokes light at the peak location, and
calculates the transmission loss from a result of the calculation.

17. The abnormality detection method according to claim 13, wherein, even when a location is present where a value of the product of the value obtained by applying the FIR filter to the intensity distribution of the Stokes light and the value obtained by applying the FIR filter to the intensity distribution of the anti-Stokes light is above a set value, the data processor determines that no abnormality is present at the location when the location is a location where a transmission loss is expected in advance.

* * * * *